(12) United States Patent
Akiyama et al.

(10) Patent No.: US 8,564,652 B2
(45) Date of Patent: Oct. 22, 2013

(54) ENDOSCOPE APPARATUS

(75) Inventors: Daisuke Akiyama, Fuchu (JP); Takeshi Suga, Hino (JP); Toshihiro Hamada, Fuchu (JP)

(73) Assignee: Olympus Medical Systems Corp., Tokyo (JP)

( * ) Notice: Subject to any disclaimer, the term of this patent is extended or adjusted under 35 U.S.C. 154(b) by 17 days.

(21) Appl. No.: 13/406,745

(22) Filed: Feb. 28, 2012

(65) Prior Publication Data

US 2012/0215066 A1    Aug. 23, 2012

Related U.S. Application Data

(63) Continuation of application No. PCT/JP2011/063350, filed on Jun. 10, 2011.

(30) Foreign Application Priority Data

Jun. 25, 2010 (JP) ................................. 2010-145252

(51) Int. Cl.
A62B 1/04 (2006.01)
A61B 1/06 (2006.01)

(52) U.S. Cl.
USPC ............................................ 348/71; 600/177

(58) Field of Classification Search
USPC ......... 348/65, 70, 71; 600/160, 177, 178, 109
See application file for complete search history.

(56) References Cited

U.S. PATENT DOCUMENTS

| | | | |
|---|---|---|---|
| 5,032,913 A * | 7/1991 | Hattori et al. | 348/70 |
| 5,111,281 A * | 5/1992 | Sekiguchi | 348/65 |
| 5,408,265 A * | 4/1995 | Sasaki | 348/70 |
| 5,864,361 A | 1/1999 | Sekiya et al. | |
| 2003/0050532 A1 | 3/2003 | Doguchi | |
| 2007/0090271 A1 | 4/2007 | Kobayashi | |

FOREIGN PATENT DOCUMENTS

| | | |
|---|---|---|
| EP | 1 294 186 A2 | 3/2003 |
| EP | 1 880 657 A1 | 1/2008 |
| JP | S61-62440 A | 3/1986 |
| JP | 8-126607 A | 5/1996 |
| JP | 9-131310 A | 5/1997 |
| JP | 10-59737 A | 3/1998 |
| JP | 11-14840 A | 1/1999 |
| JP | 2003-61905 A | 3/2003 |
| JP | 2003-79570 A | 3/2003 |
| JP | 2004-33334 A | 2/2004 |
| JP | 2006-26128 A | 2/2006 |
| JP | 2007-111338 A | 5/2007 |
| JP | 2008-86526 A | 4/2008 |
| JP | 2009-285191 A | 12/2009 |

OTHER PUBLICATIONS

European Search Report dated Jan. 21, 2013 from corresponding European Patent Application EP 11 79 7997.1.

* cited by examiner

*Primary Examiner* — Gims Philippe
(74) *Attorney, Agent, or Firm* — Scully, Scott, Murphy & Presser, P.C.

(57) ABSTRACT

In an endoscope apparatus, inside an endoscope, color correction processing is performed that performs multiplication between a color correction coefficient that is set based on a plurality of numerical apertures with respect to a plurality of different wavelengths included in a wavelength band of illuminating light of a light guide that is mounted in the endoscope and that transmits light-source light from a light source apparatus, and at least one of B, G and R signals generated by the signal processing apparatus.

5 Claims, 9 Drawing Sheets

ENDOSCOPE APPARATUS

CROSS REFERENCE TO RELATED APPLICATION

This application is a continuation application of PCT/JP2011/063350 filed on Jun. 10, 2011 and claims benefit of Japanese Application No. 2010-145252 filed in Japan on Jun. 25, 2010, the entire contents of which are incorporated herein by this reference.

BACKGROUND OF THE INVENTION

1. Field of the Invention

The present invention relates to an endoscope apparatus that observes an inside of a subject using an endoscope.

2. Description of the Related Art

Generally, an endoscope apparatus includes an endoscope that has an image pickup device for photographing in vivo tissue as an object and a light guide that transmits an illuminating light for illuminating the object, a processor as a signal processing apparatus that processes a video signal from the image pickup device inside the endoscope and outputs a processed signal to a monitor, and a light source apparatus that supplies an illuminating light to the light guide inside the endoscope.

In endoscope apparatuses of this kind, in some cases a common light source apparatus is utilized even when endoscopes of different kinds are used, such as, for example, an upper digestive tract endoscope and a lower digestive tract endoscope. Even when using endoscopes of different kinds, it is desirable that an observed image that has good color reproducibility can be displayed on a monitor.

An endoscope apparatus disclosed in Japanese Patent Application Laid-Open Publication No. 8-126607 as a first conventional example includes luminous flux control means that controls the luminous flux of light-source light that is supplied to a light guide, by means of an applied voltage of a light source lamp and a diaphragm that blocks an optical path.

According to the first conventional example, in accordance with the control state of the luminous flux of light-source light, with respect to an image signal of an endoscopic image obtained by an image pickup device, color tone correction means performs color tone correction separately for each portion of the endoscopic image that is divided into a plurality of portions (plurality of regions).

When picking up a color image under white color illuminating light that spans the visible wavelength band, for the visible wavelength band also, the numerical apertures of light guides for different wavelengths in the wavelength band have respectively different values.

Accordingly, with respect to the visible wavelength band also, if color correction is not performed in accordance with the respective numerical apertures for a plurality of respectively different wavelengths in the wavelength band, it is difficult to obtain an endoscopic image as an observation image with good color reproducibility.

In this connection, in a light source apparatus disclosed in Japanese Patent Application Laid-Open Publication No. 2006-26128 as a second conventional example, a connector section is formed to which a light guide is connected, in which a visible light source that generates visible light and an excitation light source that generates excitation light are provided, and in which optical paths of the visible light and excitation light from the two light sources are made common by an optical path synthesizing element.

The second conventional example discloses a configuration in which a luminous flux diameter produced by a condensing lens that condenses visible light is switched in accordance with a numerical aperture of a light guide of an endoscope connected to the connector section of the light source apparatus. That is, the second conventional example only discloses switching of a luminous flux diameter produced by a condensing lens that condenses light, in accordance with a numerical aperture of a light guide of an endoscope. Although conventionally, with respect to the design of endoscope apparatuses, a light guide has been selected that has an NA that conforms to a specification for the light condensing characteristics of the light source apparatus, in recent years the situation is such that light guides of various characteristics that are different from those assumed at the time of designing the endoscope apparatus are used for endoscope apparatuses that include identical light source apparatuses.

SUMMARY OF THE INVENTION

An endoscope apparatus according to one aspect of the present invention includes: an endoscope in which an image pickup device and a light guide that emits an illuminating light are mounted; a signal processing apparatus to which the endoscope is detachably connected, and which performs signal processing with respect to an output signal of the image pickup device that is mounted in the endoscope that is connected; and color correction means that performs color correction processing by performing multiplication between a color correction coefficient that is set based on a plurality of numerical apertures with respect to a plurality of different wavelengths included in a wavelength band of illuminating light of the light guide that is mounted in the endoscope that is connected, and at least one of signals of B, G and R generated by the signal processing apparatus.

DETAILED DESCRIPTION OF THE PREFERRED EMBODIMENTS

Hereunder, embodiments of the present invention are described with reference to the drawings.

(First Embodiment)

Figure 1:
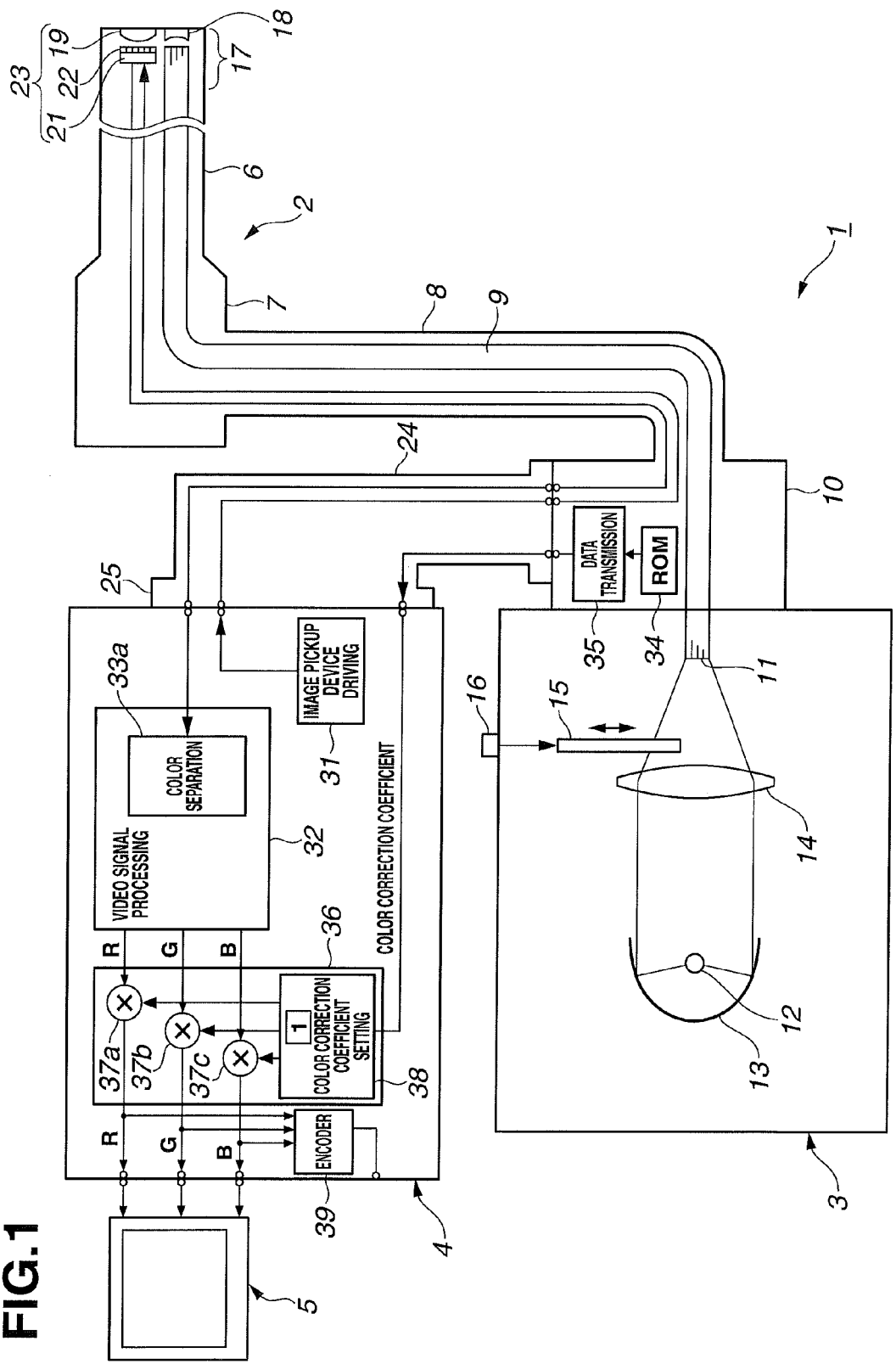
FIG. 1 is a view that illustrates an overall configuration of an endoscope apparatus according to a first embodiment of the present invention.

As shown in FIG. 1, an endoscope apparatus 1 according to a first embodiment of the present invention includes an endoscope 2 that, taking a diseased part inside a body cavity or the like as an object, picks up an image of the object and outputs an image pickup signal, a light source apparatus 3 for supplying an illuminating light to the endoscope 2, a processor 4 as a signal processing apparatus that performs signal processing of an image pickup signal from the endoscope 2, and a monitor 5 as a display apparatus that displays an image corresponding to a video signal that is outputted from the processor 4 as an endoscopic image.

The endoscope 2 has an insertion portion 6 that is inserted into a body cavity, an operation portion 7 provided at a rear end of the insertion portion 6, and a universal cable 8 that extends from the operation portion 7.

A light guide 9 that transmits light for illumination (light source-emitted light or light-source light) that is incident from the light source apparatus 3, and emits the light as illuminating light is inserted through the inside of the universal cable 8.

In a connector 10 that is provided at an end portion of the universal cable 8, a light guide connector is formed in which a light guide end face 11 that serves as an incident end portion of light-source light protrudes from the connector 10.

The light source apparatus 3 includes a parabolic mirror 13 as a reflecting mirror, and has a light source lamp 12 that generates light-source light and a condensing lens 14 as a light source optical system that condenses light-source light of substantially parallel luminous flux that is generated by reflection of the parabolic mirror 13 of the light source lamp 12 and supplies the condensed light-source light to the light guide end face 11.

A light amount diaphragm (hereunder, abbreviated to simply "diaphragm") 15 that adjusts a light-source light amount that is condensed by the condensing lens 14 is also provided in the light source apparatus 3. The diaphragm 15 can adjust a light-source light amount by, as shown by arrows in the drawing, performing an operation to move to the side of an optical path generated by the light source lamp 12 or to withdraw from the optical path in accordance with an operation of a diaphragm setting section 16.

The diaphragm 15 can move to the optical path side so that, with respect to the light-source light amount incident on the light guide end face 11, a shielded proportion of the light-source light amount increases and as a result the light-source light amount is reduced. Further, the diaphragm 15 can move so as to withdraw from the optical path to decrease the proportion of the light-source light amount that is shielded and thereby reduce the diaphragm amount.

Although a configuration example in which a light-source light amount is manually adjusted is illustrated in FIG. 1, as described in a later embodiment, a configuration may also be adopted in which the light-source light amount is automatically adjusted (subjected to light adjustment) so as to obtain an endoscopic image of an appropriate brightness that is preliminarily set.

Light-source light that is supplied from the light source apparatus 3 to the light guide 9 is transmitted by the light guide 9 inside the endoscope 2, passes through an illumination optical system 18 from a light guide distal end face disposed on the inside of an illuminating window provided in a distal end portion 17 of the insertion portion 6, and is emitted to outside as illuminating light to illuminate living tissue such as a diseased part inside a body cavity as an object.

An observation window (or an image pickup window) is provided adjacent to the illuminating window in the distal end portion 17. An objective optical system 19 is provided in the observation window, and an image pickup device 21 such as a charge coupled device (abbreviated as "CCD") is disposed at an image-formation position thereof. In this connection, a color filter 22 is provided on an image pickup surface of the image pickup device 21, and an optical image that is formed on the image pickup surface is subjected to optical color separation in respective pixel units. An image pickup section 23 as image pickup means that picks up a color image is formed by the objective optical system 19 and the image pickup device 21.

The image pickup device 21 is connected with a signal wire that is inserted through the inside of the endoscope 2. The signal wire is connected with a signal wire that is inserted through the inside of a cable 24 that extends from the connector 10. An electrical connector 25 at an end portion of the cable 24 is detachably connected to the processor 4.

The image pickup device 21 outputs a signal that has been subjected to photoelectric conversion by application of a driving signal from an image pickup device drive circuit 31 inside the processor 4. The output signal of the image pickup device 21 is inputted into a video signal processing circuit 32 provided inside the processor 4.

In the video signal processing circuit 32, signal processing is performed such as signal processing of a color separation circuit 33a that performs color separation with respect to an output signal of the image pickup device 21 in correspondence with the array structure of the color filter 22. The video signal processing circuit 32 generates color signals, for example, for three primary colors consisting of red (R), green (G) and blue (B) (that is, R, G and B signals), and outputs the color signals as video signals from the video signal processing circuit 32. Further, according to the present embodiment, each endoscope 2 includes, for example, a ROM (read only memory) 34 as information storage means that stores (data of) information that corresponds to the classifications of a plurality of numerical apertures (NA) of respective light guides 9 mounted in the respective endoscopes 2.

The endoscope 2 also has a data transmission section 35 that reads out data stored in the ROM 34 and transmits the data to the processor 4. The ROM 34 and the data transmission section 35 are provided, for example, inside the connector 10. Note that the present invention is not limited to a configuration in which the ROM 34 is provided inside the connector 10 of the endoscope 2.

When the electrical connector 25 is connected to the processor 4, data stored in the ROM 34, specifically, data regarding color correction coefficients, is outputted by the data transmission section 35 to the color correction circuit 36 that performs color correction processing that is provided inside the processor 4.

Note that the present invention is not limited to a configuration example in which the ROM 34 and the data transmission section 35 are provided on the endoscope 2 side. For example, a configuration may also be adopted in which the ROM 34 is provided in the endoscope 2, and a data read-out section that reads out data from the ROM 34 is provided on the processor 4 side.

The color correction circuit 36 includes, for example, multiplication circuits 37a, 37b and 37c, and a color correction coefficient setting circuit 38 that sets color correction coefficients that are outputted to the multiplication circuits 37a, 37b and 37c. The color correction coefficient setting circuit 38 includes, for example, a memory, and stores color correction coefficients that are transmitted from the data transmission section 35, and outputs the stored color correction coefficients to the multiplication circuits 37a, 37b and 37c.

The multiplication circuits 37a, 37b and 37c perform multiplication between R, G and B signals that are outputted from the video signal processing circuit 32 and inputted to a first input terminal and color correction coefficients on the color correction coefficient setting circuit 38 side that are inputted to a second input terminal. In the present embodiment, for example, a G signal is set to 1 as a reference color correction coefficient for R and B signals. In other words, color correction coefficients of the other color signals are normalized by taking the G signal as a reference.

In FIG. 1, an example in which the color correction coefficient for a G signal is set to 1 is schematically illustrated. When a configuration is adopted in which a G signal is set as a reference color correction coefficient, the multiplication circuit 37b can be omitted.

A configuration may also be adopted in which, instead of performing color correction with respect to R and B signals by taking a G signal as a reference on the color correction circuit 36 side, on the side of the ROM 34 that stores data for color correction coefficients, data for color correction coefficients is stored so as to perform color correction with respect to R and B signals by taking a G signal as a reference (this case is described in a description of operations hereunder).

The color correction circuit 36 performs appropriate color correction processing for R, G and B signals (more specifically, for R and B signals taking a G signal as a reference) in correspondence with an NA classification of the light guide 9 (more specifically, a plurality of NA values for a plurality of wavelengths). R, G and B signals that are outputted from the color correction circuit 36 are outputted to the monitor 5. In this connection, a configuration may also be adopted in which, for example, color correction coefficients are set that are classified into a plurality of classifications in accordance with a plurality of NA values for a plurality of wavelengths, and color correction processing is performed according to the plurality of classifications.

Furthermore, a configuration may be adopted that converts R, G and B signals into video signals of another signal form such as a composite signal or an S-video signal by means of an encoder 39 so as to correspond to a case in which the monitor 5 displays signals of a different form. The R, G and B signals that have undergone color correction (more specifically, R and B signals that have undergone color correction taking a G signal as a reference) are outputted to the monitor 5.

Even in a case in which an NA of the light guide 9 is different, the monitor 5 displays an endoscopic image as an observation image with favorable color reproducibility that has undergone appropriate color correction.

Next, the necessity of performing color correction and the operations to perform color correction are described with respect to a case in which an NA of the light guide 9 is different according to the present embodiment.

Figure 2:
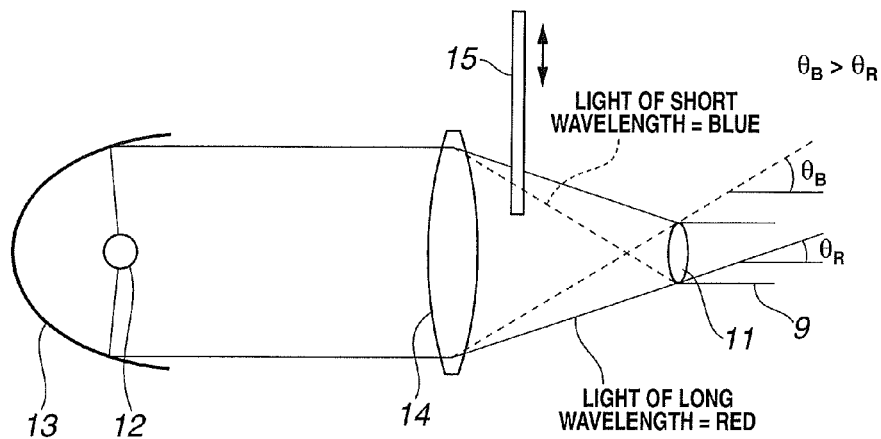
FIG. 2 is a view that illustrates a manner in which light-source light generated by a light source apparatus is supplied to a light guide end face.

FIG. 2 shows a portion of the light source apparatus 3 shown in FIG. 1 according to the present embodiment, and the light guide end face 11 of the light guide 9 that is connected to the light source apparatus 3.

With respect to the light guide 9 on which light-source light from the light source apparatus 3 is incident from the light guide end face 11 thereof, an NA exists that corresponds to an acceptable incident angle of the light-source light that is incident on the light guide 9. The NA of the light guide 9 is determined with the following equation by means of a refractive index $n_c$ of the core and a refractive index $n_k$ of the cladding of an optical fiber constituting the light guide 9. Light of an angle that is greater than an acceptance angle $\theta_i$ for the incident angle of light is not transmitted.

$$NA = \sin \theta_i = (n_c^2 - n_k^2)^{1/2}$$

Therefore, although the NA of the light guide 9 is normally set to be greater than the NA, that is, the emitted light angle, of the light source apparatus 3 to which the light guide 9 is connected, in reality light of an angle that is greater than the NA of the light source apparatus 3 is also emitted from the light source apparatus 3. Therefore, it is known that, even when using a light guide 9 that has an NA that is greater than the NA of the light source apparatus 3, if the NA of the light guide 9 is different, the amount of light that is transmitted changes.

Further, in order to efficiently condense light-source light from the light source lamp 12 into the light guide 9 inside the endoscope 2, in most cases the condensing lens 14 (in FIG. 1 and FIG. 2, illustrated in a simplified manner using a single convex lens) of the light source apparatus 3 is constituted by a positive lens group that has strong power and a small number of lens. In this configuration, depending on a chromatic aberration that is produced at a convex lens, as shown in FIG. 2, the maximum exit angle of light-source light, that is, the maximum incident angle of light that converges on the light guide end face 11 differs according to the wavelength.

In FIG. 2, for example, in a wavelength band of white color light, a maximum incident angle $\theta_B$ of light that converges on the light guide end face 11 in the case of, for example, blue as light with a short wavelength is greater than a maximum incident angle $\theta_R$ of light that converges on the light guide end face 11 in the case of, for example, red as light with a long wavelength. That is, $\theta_B > \theta_R$.

Figure 3:
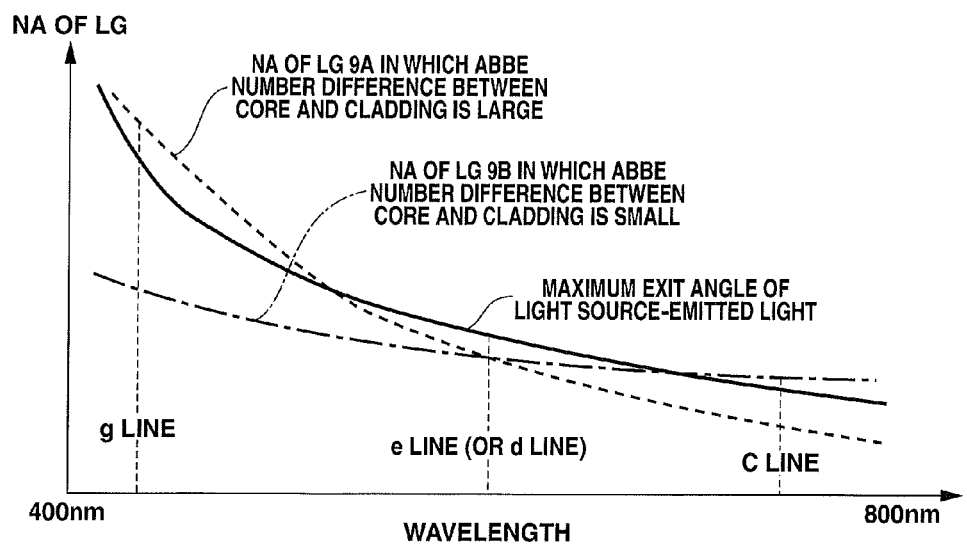
FIG. 3 is a view that illustrates an example of characteristics of numerical apertures of light guides that change according to the properties of a material.

FIG. 3 illustrates one example of a maximum emitted light angle (NA) of the light source apparatus 3 and NA characteristics of light guides in which Abbe number differences between a core and a cladding are different using a solid line, a dotted line, and an alternate long and short dashed line with respect to the visible wavelength band of white color light.

In FIG. 3, an NA in the case of a light guide 9A for which there is a large Abbe number difference between the core and the cladding, and an NA in the case of a light guide 9B for which there is a small Abbe number difference between the core and the cladding are illustrated. In the drawing of FIG. 3 and the like, the term "light guide" is abbreviated to "LG".

Note that, in FIG. 3, a g line (435.8 nm), an e line (546.1 nm) or a d line (587.6 nm), and a C line (656.3 nm) are shown as three spectral lines in the respective wavelength regions of blue, green and red.

A change, that is, dispersion, caused by a wavelength of the refractive index of glass is expressed as an Abbe number, and when a difference exists with respect to the difference between the respective Abbe numbers of a core and a cladding, as in the example of the characteristics of the two light guides 9A and 9B shown in FIG. 3, the slopes of variation curves with respect to the NA wavelengths differ. In FIG. 3, since the NA of the two light guides 9A and 9B are the same at the e line (or d line), and the relationships with the maximum exit angle of light source-emitted light (light-source light) are also the same, a proportion of green color light that is transmitted is approximately the same in the two light guides 9A and 9B.

However, when the wavelengths deviate from the e line (or d line), a difference arises between the NA of the two light guides 9A and 9B, the proportion of light that is taken in from the light source is different for each wavelength. For example, because the light guide 9A covers a major portion of light-source light in the blue bandwidth, the light guide 9A takes in a large amount of blue light from the light source and an illuminating light thereof turns blue, while in contrast, because the light guide 9B can only transmit close to half the amount of light-source light, the color of an illuminating light thereof does not turn blue.

When a group of endoscopes in which various light guides 9A and 9B whose NA differ in this manner are mounted are connected to the endoscope apparatus 1, the possibility that the color reproduction of an endoscopic image will differ depending on the endoscope increases.

Although it is possible for a user to manually adjust the color, setting an optimal color each time for each endoscope involves a large burden in terms of time and labor for the user. Therefore, according to the present embodiment, the processor 4 included in the endoscope apparatus 1 performs color correction processing to automatically enable good color reproduction in accordance with the NA of the light guide that is mounted in the endoscope. More specifically, according to the present embodiment, with respect to the influence on illumination that is due to transmission characteristics of light having wavelength dependence according to the NA of the light guide 9, the aforementioned influence that is due to the transmission characteristics according to the NA of the light guide 9 are eliminated by performing color correction using color correction coefficients for R, G and B signals obtained by picking up a color image that are outputted from the image pickup device 21 included in the image pickup means.

The endoscope apparatus 1 of the present embodiment according to this configuration has the endoscope 2 in which the image pickup device 21 and the light guide 9 that emits an illuminating light are mounted, and the processor 4 to which the endoscope 2 is detachably connected and which serves as a signal processing apparatus that performs signal processing with respect to signals obtained by an image pickup operation by the image pickup device 21 that is mounted in the endoscope 2 connected thereto.

A feature of the endoscope apparatus 1 is that the endoscope apparatus 1 includes the ROM 34 as information storage means that stores information corresponding to classifications of a plurality of numerical apertures with respect to a plurality of different spectral lines included in a wavelength band of the illuminating light with respect to the light guide 9 that is detachably connected to the light source apparatus 3, and the color correction circuit 36 as color correction means that is provided in the signal processing apparatus and that, based on the information, performs color correction processing with respect to an output signal of the image pickup device 21 in accordance with the classifications of the plurality of numerical apertures for the plurality of different spectral lines with respect to the light guide 9.

Next, operations of the present embodiment are described. When performing endoscopy, a surgeon as the user of the endoscope apparatus 1 connects the endoscope 2 to the light source apparatus 3 and the processor 4 as shown in FIG. 1. Thereupon, data of the ROM 34 that stores data corresponding to a plurality of NA for a plurality of wavelengths of the light guide 9 that is mounted in the endoscope 2 is read out by the data transmission section 35 and transmitted to the color correction circuit 36 inside the processor 4.

As described above, data for color correction coefficients that are calculated based on three NA at the g line, the e line, and the C line of the light guide 9 that is mounted in the endoscope 2 is stored inside the ROM 34.

As a more specific example, cases will now be described in which, for example, an endoscope 2A is used as the endoscope 2, and an endoscope 2B is used as the endoscope 2. It is assumed that the endoscope 2A has the light guide 9A, and the endoscope 2B has the light guide 9B. The light guides 9A and 9B have NA of different classifications.

When the light guide 9A is mounted in the endoscope 2A, a B signal correction coefficient and an R signal correction coefficient corresponding to the light guide 9A are stored in the ROM 34. In contrast, when the light guide 9B is mounted in the endoscope 2B, a B signal correction coefficient and an R signal correction coefficient corresponding to the light guide 9B are stored in the ROM 34.

B signal correction coefficient of light guide 9A=1.00
R signal correction coefficient of light guide 9A=1.00
B signal correction coefficient of light guide 9B=1.08
R signal correction coefficient of light guide 9B=0.96

The optical characteristics of the light guide 9A and the light guide 9B are as follows.

Light guide 9A: core $n_e$=1.643, $v_e$=59.8
cladding $n_e$=1.51, $v_e$=59.3
$NA_g$=0.649, $NA_e$=0.642, $NA_c$=0.638
Light guide 9B: core $n_e$=1.652, $v_e$=33.5
cladding $n_e$=1.52, $v_e$=59.0
$NA_g$=0.672, $NA_e$=0.641, $NA_c$=0.626

The above described color correction coefficients are determined by the following equations.

$$B \text{ signal correction coefficient} = (NA_g/NA_e/\alpha_B) \quad (1)$$

$$R \text{ signal correction coefficient} = (NA_c/NA_e/\alpha_R) \quad (2)$$

To ensure that a reference for correction processing or color reproduction of an image is not itself complicated, $\alpha_B$ and $\alpha_R$ in equation (1) and equation (2) are defined by selecting a light guide to serve as a reference for colors among light guides connected to or that may be connected to the endoscope apparatus 1, and defining $\alpha_B$ and $\alpha_R$ so that each color correction coefficient of the light guide becomes 1. In the present embodiment, color correction coefficients are set for both the light guide 9A and the light guide 9B using $\alpha_B$ and $\alpha_R$ based on the following equations.

$$\alpha_B = (NA_g \text{ of light guide } 9A)/(NA_e \text{ of light guide } 9A) = 1.011$$

$$\alpha_R = (NA_c \text{ of light guide } 9A)/(NA_e \text{ of light guide } 9A) = 0.994$$

Further, β in equation (1) and equation (2) is determined by experiment in accordance with an emitted light spectrum that depends on the chromatic aberration and light distribution characteristics of the condensing lens 14 as a light source optical system as well as the light source lamp 12 of the light source apparatus 3 to which the endoscope 2 is connected. According to the present embodiment, β=2.

In the present embodiment, a reference wavelength that is generally used as an NA is approximately the same for both of the light guides 9A and 9B. However, because NA are different in a wavelength region of blue (g line) and a wavelength region of red (C line), the respective colors (color balance) of light irradiated onto an object inside a body cavity from the respective light guides 9A and 9B will be different.

The above described color correction coefficients are read into the color correction circuit 36 inside the processor 4 through the data transmission section 35. Inside the processor 4, a signal outputted from the image pickup device 21 of the endoscope 2 is separated into R, G and B signals by the color separation circuit 33a of the video signal processing circuit 32. After the R, G and B signals have undergone signal processing such as γ correction or edge enhancement, the video signal processing circuit 32 outputs the R, G and B signals to the color correction circuit 36. Multiplication circuits 37a and 37c inside the color correction circuit 36 perform color correction by multiplying the R signal by the R signal correction coefficient and multiplying the B signal by the B signal correction coefficient.

The R, G and B signals as video signals that have undergone color correction are outputted to the monitor 5, or are converted into a signal form that is compatible with the monitor 5 and thereafter outputted to the monitor 5. Thus an endoscopic image that retains good color reproduction is displayed as an observation image on the display surface of the monitor 5. Thus, the surgeon can observe an endoscopic image that retains good color reproduction.

According to the present embodiment configured in this manner, color reproduction of an endoscopic image as an observation image can also be appropriately performed when using endoscopes 2 (as a specific example, endoscopes 2A and 2B) in which the numerical aperture (NA) of the light guide 9 differs for a plurality of wavelengths in a wavelength band of illuminating light.

Accordingly, because the surgeon can observe an endoscopic image in a state in which the color reproduction thereof is favorable, it is possible for the surgeon to smoothly perform diagnosis regarding the symptoms of a lesion part or the like. Further, according to the present embodiment, only by performing color correction processing that multiplies R, G and B signals or R and B signals by one color correction coefficient, respectively, color correction with good color reproducibility can be carried out simply. That is, color correction with good color reproducibility can be performed only by using three or two color correction coefficients. Therefore, color correction can be performed with a low cost and simple configuration.

Figure 4:
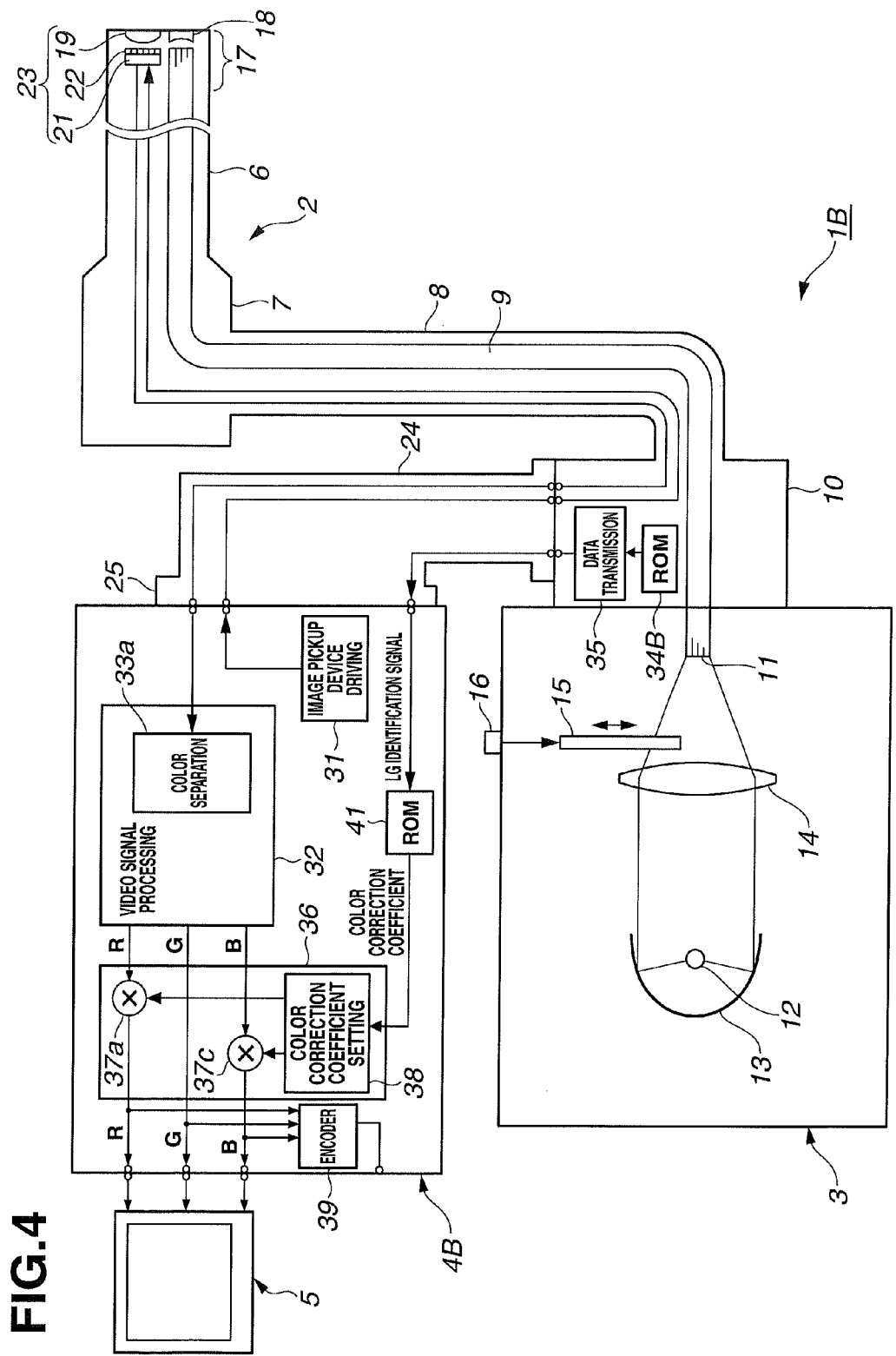
FIG. 4 is a view that illustrates an overall configuration of an endoscope apparatus according to a first modification example of the first embodiment.

FIG. 4 shows an endoscope apparatus 1B according to a first modification example of the first embodiment. Although in the endoscope apparatus 1 shown in FIG. 1 a configuration is adopted that transmits (outputs) data for color correction coefficients from the endoscope 2 to the processor 4, a configuration may also be adopted that, as in the present modification example shown in FIG. 4, outputs a light guide identification signal (or light guide classification signal) corresponding to a (classification of the) NA of the light guide 9 that is mounted in the endoscope 2.

In this case, a ROM 34B provided in the endoscope 2 stores data for a light guide identification signal that corresponds to a value or a classification of an NA of the light guide 9. For example, an identification number or an identification code that is unique to the endoscope may be utilized as the data. In this case, it is favorable to adopt a configuration such that a classification of an NA of a light guide can be known from one part of the identification number.

In the present modification example, a processor 4B has a ROM 41 in which data for color correction coefficients corresponding to an NA that corresponds to a light guide identification signal is stored based on the light guide identification signal. By utilizing a light guide identification signal as, for example, a readout signal (address signal), the processor 4B reads out data for color correction coefficients corresponding to the light guide identification signal from the ROM 41 and outputs the data to the color correction coefficient setting circuit 38. Note that a configuration may also be adopted in which the ROM 41 is provided inside the color correction circuit 36.

In the configuration example shown in FIG. 4, a configuration that does not have the multiplication circuit 37b is shown. The remaining configuration is the same as the configuration shown in FIG. 1.

The present modification example has almost the same advantageous effects as those of the endoscope apparatus 1 shown in FIG. 1. Further, as described above, a configuration may also be adopted in which only the ROM 34B is provided on the endoscope 2 side, and a circuit that reads out data of the ROM 34B is provided on the processor 4B side.

According to the present modification example, there is the advantage that the endoscope apparatus can also be widely applied to existing endoscopes that include unique identification information. That is, by registering data for color correction coefficients corresponding to an NA of a light guide mounted in an existing endoscope in association with unique identification information of the endoscope in the ROM 41 on the processor 4B side, the endoscope apparatus can be simply made to correspond to an existing endoscope also.

In this connection, a configuration may also be adopted that, instead of the ROM 41, includes a plurality of storage sections that store data for color correction coefficients corresponding to a classification of the NA of respective light guides, respectively, and a switch that switches to (selects) a corresponding single storage section from among the plurality of storage sections, and that, by means of a light guide identification signal, selects a storage section that outputs data for color correction coefficients that correspond to a classification of an NA of a light guide.

Figure 5:
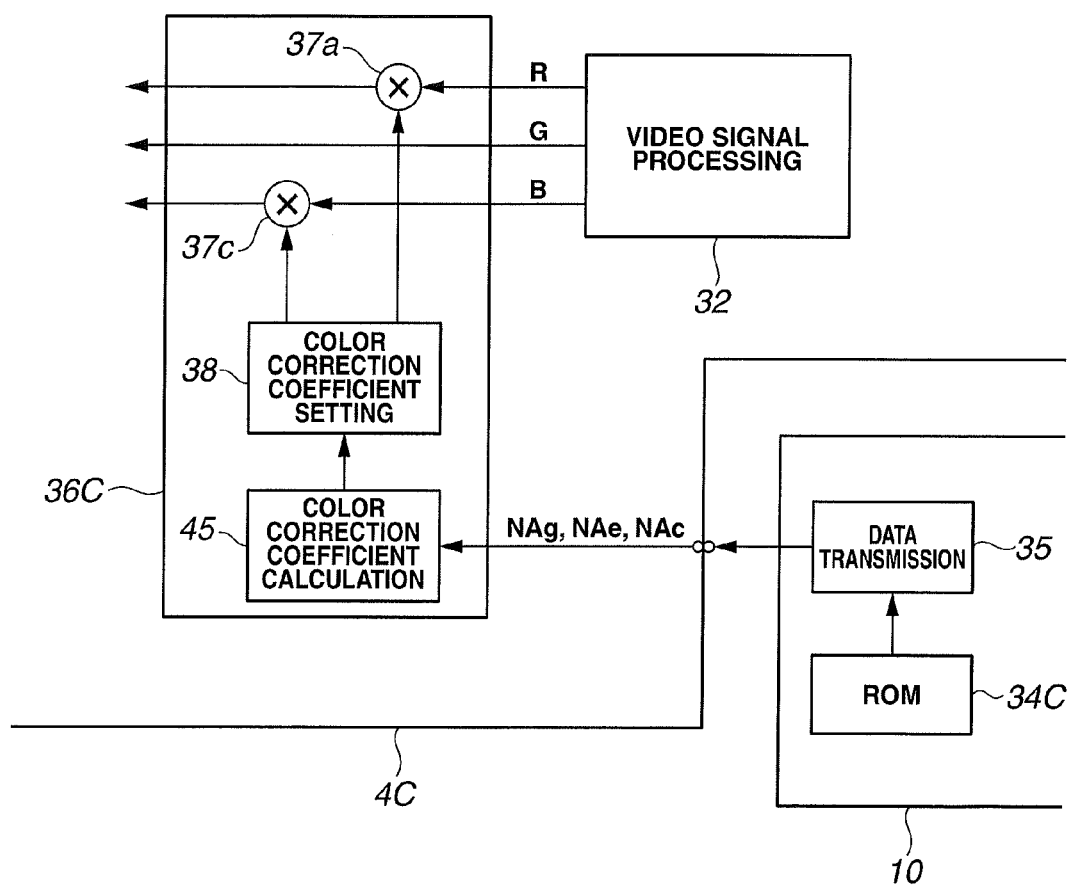
FIG. 5 is a view that illustrates a configuration at the periphery of a color correction circuit according to a second modification example of the first embodiment.

A configuration shown in FIG. 5 may be adopted as a second modification example. FIG. 5 illustrates the configuration at the periphery of a color correction circuit 36 according to the second modification example. The data transmission section 35 provided, for example, inside the connector 10 of the endoscope 2 that is connected to a processor 4C in the present modification example transmits respective NA values at the g line, e line, and C line (that is, $NA_g$, $NA_e$ and $NA_c$) of the light guide 9 mounted in the endoscope 2 to the processor 4C, instead of a light guide identification signal stored in a ROM 34C or as a light guide identification signal.

In this case, for example, a color correction circuit 36C inside the processor 4C includes therein a color correction coefficient calculation circuit 45 that calculates color correction coefficients. The color correction coefficient calculation circuit 45 calculates color correction coefficients by means of the above described equation (1) and equation (2).

The calculated color correction coefficients are sent to the color correction coefficient setting circuit 38. The color correction coefficient setting circuit 38 performs color correction as shown in FIG. 1 and FIG. 4 and the like by setting color correction coefficients for multiplication in the multiplication circuits 37a and 37c. In the present modification example, the color correction circuit 36C performs calculation of color correction coefficients and color correction. The present modification example also has almost the same advantageous effects as those of the first embodiment.

Figure 6:
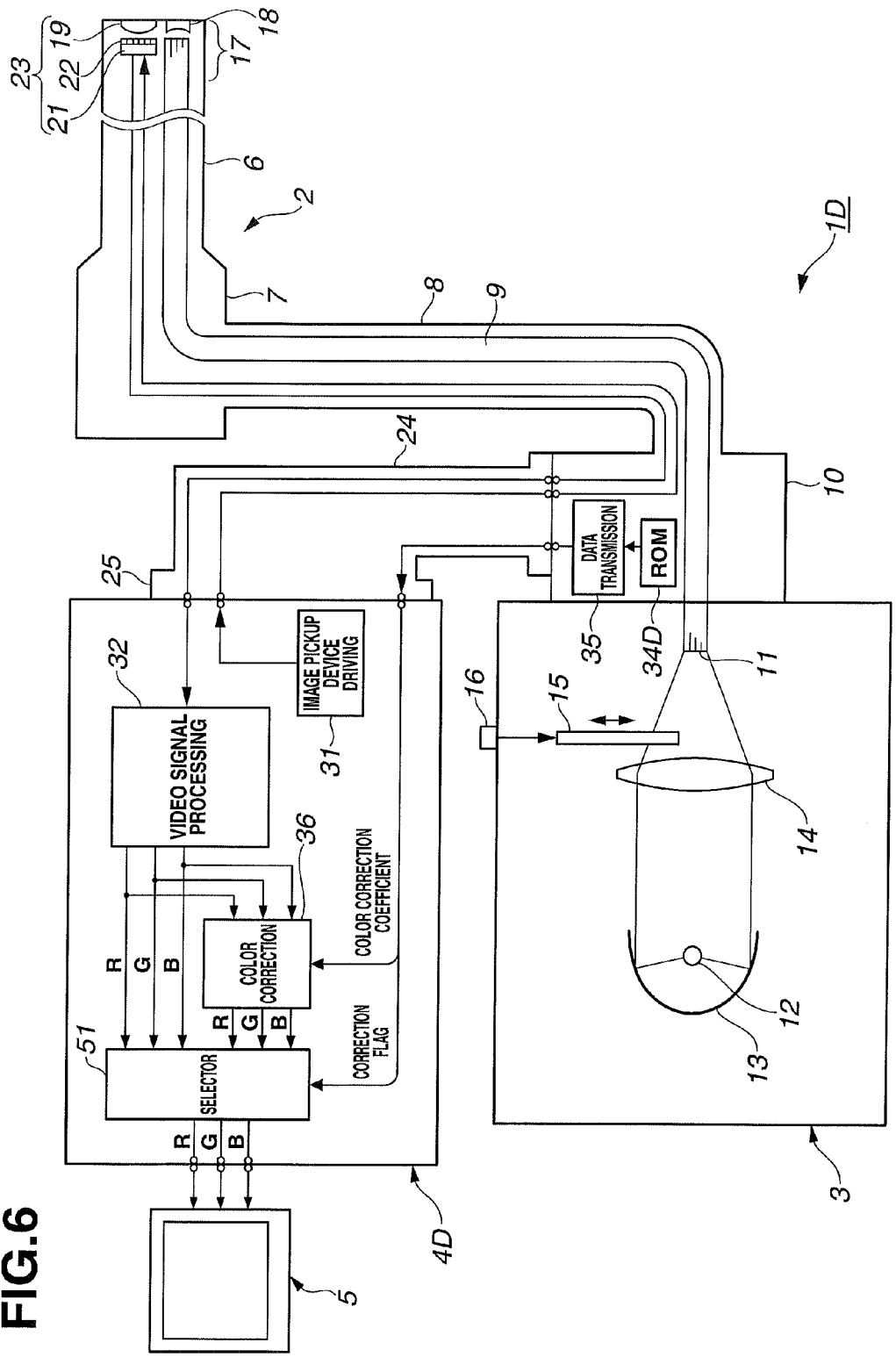
FIG. 6 is a view that illustrates an overall configuration of an endoscope apparatus according to a third modification example of the first embodiment.

FIG. 6 shows an endoscope apparatus 1D according to a third modification example. In the present modification example, a ROM 34D provided in the endoscope 2 stores data for color correction coefficients corresponding to a classification of an NA of the light guide 9, and a correction flag that serves as a selection signal for substantially enabling or disabling color correction by the color correction circuit 36 in accordance with a range of the color correction coefficients or the like.

The data transmission section 35 outputs color correction coefficients that are read out from the ROM 34D to the color correction circuit 36 inside a processor 4D, and also outputs a correction flag to a selector 51 provided in the processor 4D.

In the processor 4D of the present modification example, the video signal processing circuit 32 outputs R, G and B signals to an input terminal of the selector 51 through the color correction circuit 36, and also outputs the R, G and B signals to another input terminal of the selector 51 without sending the R, G and B signals through the color correction circuit 36.

The selector 51 can be switched so as to select the input signals that are inputted to one of the two input terminals, by means of a binary signal of the correction flag (for example, a signal with an H level that enables correction, and an L level that disables correction). The input signals that are switched to by the selector 51 are output to the monitor 5 side as output signals.

For example, in a case in which a color correction coefficient diverges significantly from 1, the correction flag is set so as to control switching of the selector 51 so as to select signals that have undergone color correction by the color correction circuit 36.

In contrast, there are cases where color correction need not be performed when a color correction coefficient does not deviate to a great extent from 1 (is within a predetermined range). In such a case, the correction flag is set so as to select signals that do not undergo color correction. The remaining configuration is, for example, the same as the configuration in FIG. 1 or FIG. 4.

It is also possible to adopt a configuration that allows the correction flag to be set to either setting in accordance with the preference of the surgeon. Accordingly, if the surgeon sets the correction flag so as not to perform color correction in a case where a color correction coefficient does not deviate significantly from 1, an output signal of the video signal processing circuit 32 can be outputted to the monitor 5 side in a state in which the output signal has not undergone color correction.

In addition, a configuration may be adopted that, in accordance with the extent of a range of color correction coefficients, allows a user such as a surgeon to select the setting of the correction flag, or does not allow the user to select the setting, that is, makes a setting such that the correction flag cannot be changed. Further, in addition to the above described normal observation mode that performs normal observation in a visible region, a configuration may be adopted in which the setting of the correction flag can be changed in the case of another observation mode that is different from the normal observation mode, as in an embodiment that is described later herein.

The present modification example can widen the range of selection choices of a user in relation to the functions of the color correction circuit 36. In addition, the present modification example has the same advantageous effects as those of the first embodiment.

(Second Embodiment)

Figure 7:
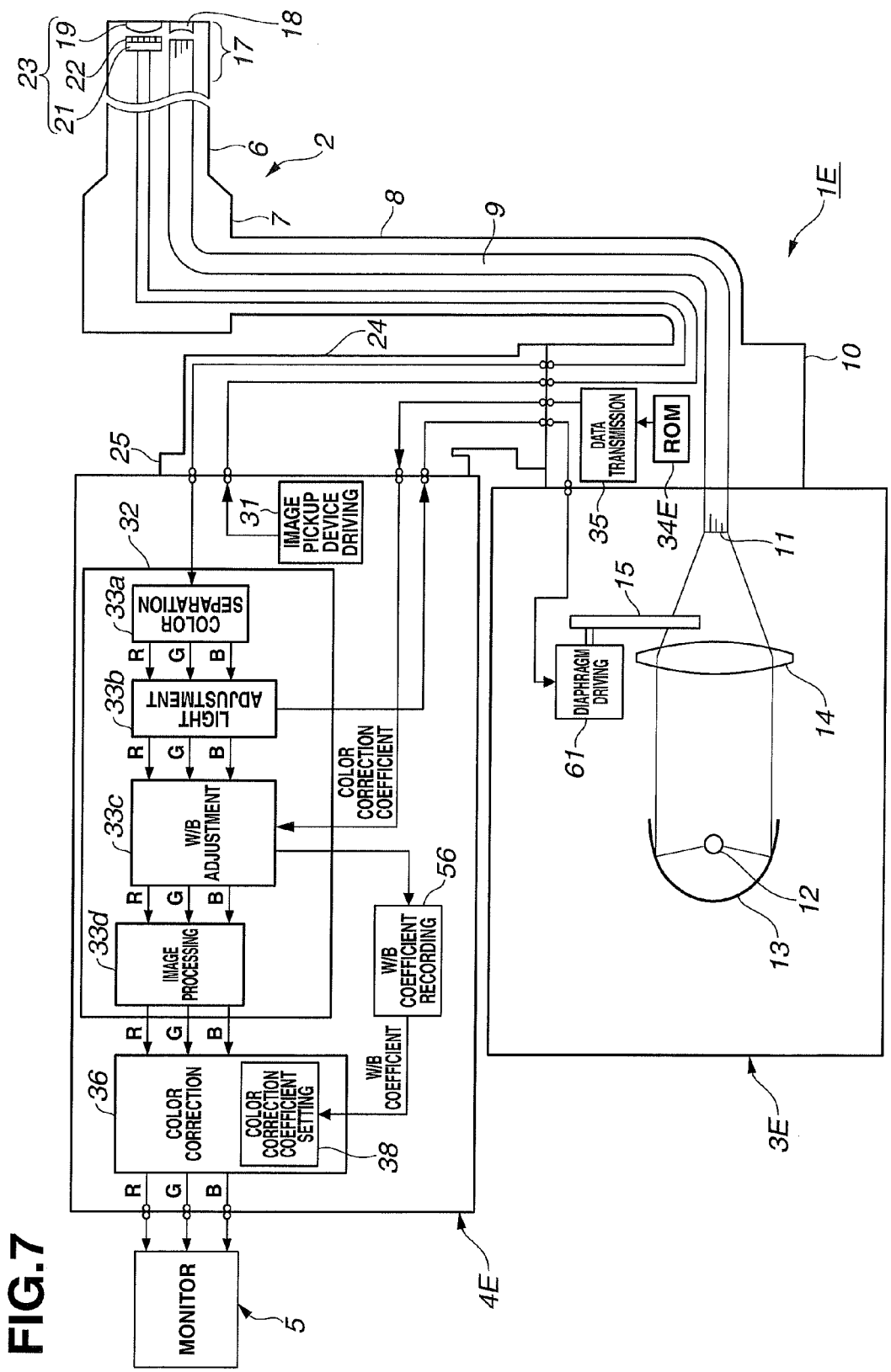
FIG. 7 is a view that illustrates an overall configuration of an endoscope apparatus according to a second embodiment of the present invention.

FIG. 7 shows an endoscope apparatus 1E according to a second embodiment of the present invention. A processor 4E according to the present embodiment has, in addition to the color separation circuit 33a, for example, a light adjustment circuit 33b that generates a light adjustment signal for automatically adjusting (light adjustment) a light-source light amount (or illuminating light amount) inside the video signal processing circuit 32.

The video signal processing circuit 32 also includes a white balance adjustment circuit 33c that determines a white balance coefficient based on color information of a video signal when an image of a white object is picked up and performs white balance adjustment in accordance with a white balance adjustment instruction from a user, and an image processing circuit 33d that performs image processing such as y correction. Note that, in the drawings, the term "white balance" is abbreviated as "W/B".

According to the present embodiment, using a white balance coefficient, the color correction circuit 36 performs color correction of a color signal to a target value of white balance adjustment. For this purpose, the processor 4E includes a white balance coefficient recording section 56 that records a white balance coefficient determined by the white balance adjustment circuit 33c, and outputs the white balance coefficient to a color correction coefficient setting circuit 38 in the color correction circuit 36.

The color correction circuit 36 uses the white balance coefficient as a color correction coefficient to perform color correction processing in the same manner as in the case of the color correction coefficients described above. By performing color correction processing using a white balance coefficient in this manner, a white object can be displayed as an image of a white object.

In this connection, the white balance adjustment circuit 33c and the white balance coefficient recording section 56 may be provided inside the video signal processing circuit 32 or inside the color correction circuit 36.

At a time of a white balance adjustment instruction that is set in a state in which an image of a white object is picked up, as white balance coefficients, the white balance adjustment circuit 33c calculates values obtained, for example, by multiplying color correction coefficients stored in a ROM 34E by the values of R, G and B signals that are inputted (in practice, the white balance coefficients are calculated for R and B signals by taking a G signal as a reference).

Thus, according to the present embodiment, color correction coefficients stored in the ROM 34E serve as color correction information that is used for calculating white balance coefficients as target values for white balance adjustment.

An output signal of the video signal processing circuit 32 is outputted to the monitor 5 through the color correction circuit 36 that performs color correction processing.

The light adjustment circuit 33b generates a luminance signal based on R, G and B signals obtained by color separation, and outputs a signal of a difference value obtained when the luminance signal is compared with a brightness target value inside the light adjustment circuit 33b to a light source apparatus 3E as a light adjustment signal. In this connection, the brightness target value is set to a mean value of luminance signals in the case of an endoscopic image with which diagnosis and observation can be carried out with ease at an appropriate brightness.

The above described light adjustment signal drives a diaphragm drive circuit 61 that varies a diaphragm amount (opening amount) of the diaphragm 15 in the light source apparatus 3E by, for example, rotating the diaphragm 15.

For example, if a luminance level of a mean value of luminance signals generated based on signals obtained as the result of an image pickup operation by the image pickup device 21 is higher than a brightness target value, the light adjustment signal is used to reduce (an opening amount) of the diaphragm 15, that is to perform light adjustment (light amount adjustment) through the diaphragm drive circuit 61 so as to narrow the diaphragm 15. In contrast, when a luminance level of a mean value of luminance signals generated based on signals obtained as the result of an image pickup operation by the image pickup device 21 is lower than a brightness target value, the light adjustment signal is used to perform light adjustment through the diaphragm drive circuit 61 so as to increase the opening amount of the diaphragm 15.

According to the present embodiment, a light adjustment signal is generated based on an output signal of the image pickup device 21, and a light-source light amount by the light source apparatus 3E is automatically adjusted in accordance with the light adjustment signal so that an endoscopic image of a brightness that is suitable for observation is obtained.

The diaphragm 15, for example, is formed by a disk-shaped light shielding plate in which a substantially wedge-shaped notch is provided on a distal end side of a shank portion, and the opening amount produced by the notch that faces onto the optical path is changed by causing the shank portion side to rotate by means of the diaphragm drive circuit 61.

In this case, a light-source light amount that is incident on the light guide end face 11 depends on a shape formed between a shade portion and a notch portion of the diaphragm 15. Further, in this case, the emission light intensity of light-source light that is condensed by the above described condensing lens 14 and emitted towards the light guide end face 11 changes according to the wavelength.

Figure 8:
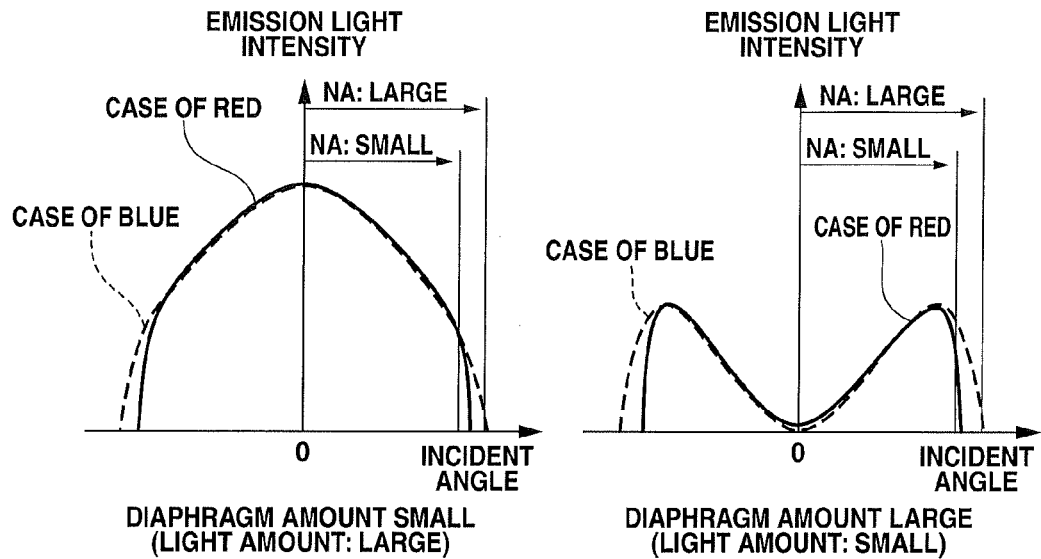
FIG. 8 is a view that illustrates an example of characteristics of the emission light intensity of light-source (emitted) light that is supplied to a light guide end face from a light source apparatus in a case of a small diaphragm amount and a case of a large diaphragm amount.

FIG. 8 shows an example of light distribution characteristics of red and blue light-source light that is supplied (emitted) to the light guide end face 11 in a case that uses the diaphragm 15 that, normally, is widely adopted. The solid lines and dashed lines in FIG. 8 illustrate light distribution characteristics in the case of red and blue light-source light, respectively. Further, the axis of abscissa represents an incident angle at which light is incident on the light guide end face 11, and the axis of ordinates represents emission light intensity.

Further, FIG. 8 shows the radiant intensity that is irradiated onto the light guide end face 11 when the diaphragm amount is small, that is, in a state in which the diaphragm amount is small and a light-source light amount is increased, and when the diaphragm amount is large, that is, in a state in which the light-source light amount is reduced. FIG. 8 shows that there is a tendency such that, in a range in which the incident angle is small, the wavelength dependence (which changes depending on a wavelength of red that is a long wavelength and a wavelength of blue that is a short wavelength as emission light intensity characteristics) is relatively small, while in a range in which the incident angle is large, the wavelength dependence increases.

When the diaphragm amount shown on the left side in FIG. 8 is small, the emission light intensity in a range in which the incident angle is small and the wavelength dependence is also comparatively small is large, and the emission light intensity in a range in which the incident angle is large and the wavelength dependence is also large is small.

In contrast, when the diaphragm amount shown on the right side in FIG. 8 is large, in a state in which the light-source light amount has been set to a small state, the emission light intensity is comparatively small in a range in which the incident angle is small and the wavelength dependence is also comparatively small, and the emission light intensity is comparatively large in a range in which the incident angle is large and the wavelength dependence is also large. In this case, the influence of the wavelength dependence increases compared to the case in which the diaphragm amount is small.

Therefore, for example, with respect to the case of a light guide having a small NA and the case of a light guide having a large NA that are shown in FIG. 8, it is necessary to take the wavelength dependence into consideration particularly when the diaphragm amount is large, more so than when the diaphragm amount is small.

Figure 9:
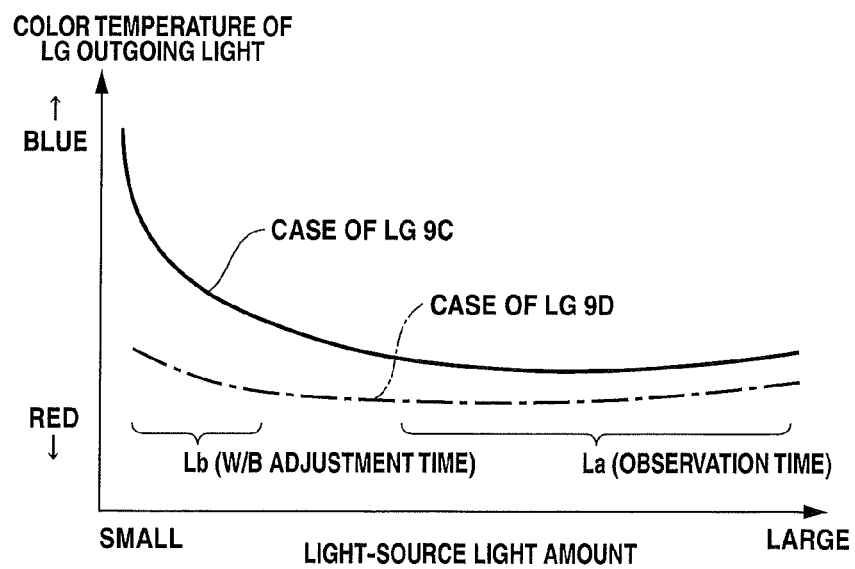
FIG. 9 is a view that illustrates an example of characteristics of the color temperature of outgoing light of light guides.

FIG. 9 illustrates an example of color temperature characteristics of outgoing light of light guides (that is, illuminating light) in a case where light-source light supplied from the light source apparatus 3 is transmitted by a light guide and is emitted as illuminating light to an object side from an illuminating window.

In this connection, the axis of abscissa shows the size of a light-source light amount (which depends on the diaphragm 15), and the axis of ordinates shows the color temperature of outgoing light of the light guide. Further, the solid line and the alternate long and short dashed line show an example of color temperature characteristics in the case of a light guide 9C with a large NA and the case of a light guide 9D with a small NA. As will be understood from FIG. 9, the color temperature varies depending on the light-source light amount, and in particular, the variation is large in a region in which the light-source light amount is small (low).

When observing an object in the body using the endoscope 2 in a state in which a light-source light amount is automatically adjusted or when a light-source light amount is set so as to obtain an endoscopic image of an appropriate brightness, since the surface of living tissue is the object of observation, there are many cases in which the light-source light amount is an amount in a range La as indicated by "observation time" in FIG. 9.

In contrast, at the time of white balance adjustment, a white object with high reflectance (that is, a bright object) is employed as a reference object for white balance adjustment. Since operations are performed by projecting a white object on a screen when performing white balance adjustment in this manner, in order to project the white object without saturation, the light source apparatus 3 enters a state in which the light-source light amount thereof is suppressed to a lower amount than at a time of normal observation. Thus, the light-source light amount is an amount in a range Lb as indicated by "white balance adjustment time" in FIG. 9.

In the conventional example, at the time of white balance adjustment, levels of R, G and B signals are set by a white balance adjustment circuit so as to display a white object that is a reference object as a white image. However, as shown in FIG. 9, since a light-source light amount at the time of white balance adjustment is considerably less than a light-source light amount at the time of actual observation, the color temperature thereof is a value that deviates from the state of the color temperature at the time of observation. Consequently, it is necessary to perform white balance adjustment while taking into consideration the amount of deviation from the color temperature at the time of observation at which observation is actually performed.

Therefore, in the present embodiment, white balance adjustment (that differs from normal) is performed so as to correct the amount by which a color temperature at the time of white balance adjustment deviates from a color temperature at the time of observation in accordance with the NA of the light guide 9, and in a case where an image of a white object is picked up in a state in which a light-source light amount is an amount at an observation time, color correction is performed so as to reproduce color of the image as an image of a white object.

The color correction method is described hereunder using FIG. 9. The state in the case of the range La of the light-source light amount at an observation time in FIG. 9 is taken as a first observation state in which an image of a white object is being picked up.

In the first observation state, when it is assumed that the signal levels (signal strengths) of R, G and B signals become, for example, Ra, Ga and Ba, in order to perform correction (for example, by multiplication) so that color reproduction of a white object as an image of a white object can be performed, white balance coefficients $C_R a$, $C_G a$ and $C_B a$ that are values such that $Ra \times C_R a = Ga \times C_G a = Ba \times C_B a = 1$ must be calculated by white balance adjustment.

In contrast, at the time of white balance adjustment, in the range Lb in FIG. 9, the state is a second observation state in which an image of a white object is being picked up. In the second observation state, when it is assumed that the signal levels (signal strengths) of R, G and B signals become, for example, Rb, Gb and Bb, in order to perform calculation based on Rb, Gb and Bb so that white balance coefficients become $C_R a$, $C_G a$ and $C_B a$, it is necessary to preliminarily set coefficients $C_R b$, $C_G b$ and $C_B b$ so that $C_R a = C_R b / Rb$, $C_G a = C_G b / Gb$, and $C_B a = C_B b / Bb$ are satisfied.

It is sufficient to preliminarily store coefficients corresponding to $C_R b$, $C_G b$ and $C_B b$ as color correction coefficients in the ROM 34E. In practice, by normalizing with the G signal, it is sufficient to store two color correction coefficients that are for the R signal and the B signal.

Thus, the ROM 34E as information storage means stores color correction coefficients as color correction information for enabling color reproduction as an image of a white object in a case where an image of a white object is picked up at the time of observation based on information for a signal intensity ratio among R, G and B signals that is obtained at a time of white balance adjustment.

Further, based on the color correction information and R, G and B signals based on an output signal of the image pickup device 21 in a state with a light-source light amount for a time of white balance adjustment, white balance coefficients that can cause white balance to be achieved in a state with a light-source light amount for a time of observation can be calculated as color correction coefficients.

The remaining configuration is the same as in the above described embodiments.

Next, operations of the present embodiment are described. In the following description, the endoscope 2 in which the light guide 9C shown in FIG. 9 is mounted is described as "endoscope 2C", and the endoscope 2 in which the light guide 9D shown in FIG. 9 is mounted is described as "endoscope 2D."

Color correction coefficients that are derived from NA at the g line, e line and C line of light guides 9C and 9D that are mounted in the endoscopes 2C and 2D and the like are stored inside the ROM 34E of the endoscopes 2C and 2D.

The specific values are as described below. When the light guide 9C is mounted in the endoscope 2C, the B signal correction coefficient and R signal correction coefficient of the light guide 9C are stored inside the ROM 34E of the endoscope 2C. When the light guide 9D is mounted in the endoscope 2D, the B signal correction coefficient and R signal correction coefficient of the light guide 9D are stored inside the ROM 34E of the endoscope 2D.

B signal correction coefficient of light guide 9C=1.00
R signal correction coefficient of light guide 9C=1.00
B signal correction coefficient of light guide 9D=0.93
R signal correction coefficient of light guide 9D=1.04

The optical characteristics of the light guide 9C and light guide 9D are as follows.

Light guide 9C: core $n_e$=1.652, $v_e$=33.5
cladding $n_e$=1.51, $v_e$=62.2
$NA_g$=0.696, $NA_e$=0.665, $NA_c$=0.649
Light guide 9D: core $n_e$=1.620, $v_e$=60.0
cladding $n_e$=1.49, $v_e$=64.2
$NA_g$=0.639, $NA_e$=0.631, $NA_c$=0.626
Further, the following values are used for $\alpha_B$, $\alpha_R$ and $\beta$.
$\alpha_B$=($NA_g$ of light guide 9C)/($NA_e$ of light guide 9C)=1.047
$\alpha_R$=($NA_c$ of light guide 9C)/($NA_e$ of light guide 9C)=0.977
$\beta$=2

According to the present embodiment, when a white balance adjustment instruction is given by a user operation, the white balance adjustment circuit 33c reads out color correction coefficients stored in the ROM 34E in the endoscope 2 through the data transmission section 35.

White balance adjustment is originally processing that calculates color correction amounts that video signals should be corrected with so that a white object that is photographed by a user is displayed as white, and applies the calculated color correction amounts to video signals from the white balance adjustment circuit 33c onwards.

However, as described in the foregoing, since the light source apparatus 3E suppresses the light-source light amount at a time of white balance adjustment to a level that is lower than at a time of observation, this changes the angle characteristics of light that is incident on the light guide and the color balance. Further, when characteristics that depend on the NA of the light guide are taken into consideration, the color of illuminating light that passes through the light guide and is emitted to the object side changes as shown in FIG. 9 in accordance with changes in the light-source light amount supplied from the light source apparatus 3E.

Although the light-source light amount is adjusted to a small light amount at the time of white balance adjustment, the light-source light amount is adjusted to a light amount that requires a larger light amount when performing observation, and consequently a difference arises in the color of illuminating light (the color temperature changes) between the time of white balance adjustment and the time of observation depending on the characteristics of the light guide.

Therefore, at a time of white balance adjustment, even if white balance adjustment is performed so as to merely reproduce a white object in the same color so as to be a white object image, as shown in FIG. 9, the problem arises that different color reproduction is performed at the time of observation depending on the NA characteristics of the light guide 9.

Therefore, according to the present embodiment, white balance coefficients in the case of performing white balance adjustment in a state with a light-source light amount for an observation time are calculated using R, G and B signals that are obtained in a state with a light-source light amount for a time of white balance adjustment, and color correction processing is performed by the color correction circuit 36 by employing the calculated white balance coefficients as color correction coefficients.

For example, in contrast to the conventional case in which a signal intensity ratio among R, G and B signals that are outputted from the white balance adjustment circuit 33c is adjusted by white balance adjustment so as to be a ratio of R:G:B=1:1:1, that is, to become white, according to the present embodiment, by purposely adjusting so as to obtain a color that is different from white when performing white balance adjustment, color reproduction that is the same as the color reproduction of the light guide that serves as a reference is performed at the time of observation, that is, a white object is reproduced as a white image.

According to the present embodiment, for example, when the endoscope 2D in which the light guide 9D is mounted is connected, white balance coefficients are calculated by which the original video signals should be multiplied so that the video signals of a white object become values such that R:G:B=0.93:1:1.04 is satisfied when performing white balance adjustment.

After the calculated white balance coefficients are recorded in the white balance coefficient recording section 56, the white balance coefficients are sent to the color correction circuit 36, and video signals from that point onwards are subjected to color correction processing based on the white balance coefficients. Subsequently, for example, R, G and B signals as video signal that have undergone color correction by the color correction circuit 36 are outputted to the monitor 5.

According to the present embodiment that operates in this manner, similarly to the first embodiment, even when using an endoscope in which the numerical aperture of the light guide differs over a wavelength band of illuminating light, an endoscopic image as an observation image with good color reproduction is obtained.

In addition, according to the present embodiment, by performing white balance adjustment, it is possible to achieve color reproduction of a white object as an image of a white object at the time of observation also.

Furthermore, according to the present embodiment, by performing white balance adjustment, it is possible to correct variations in spectral characteristics and the like that depend on the image pickup device 21. More specifically, spectral characteristics differ according to the image pickup device 21 mounted in the endoscope 2, and in particular according to the kind of the color filter 22 that is used as an optical filter.

Therefore, by performing white balance adjustment as in the present embodiment, variations in spectral characteristics of the image pickup device 21 can be corrected as described above. In other words, color correction coefficients that are used by the color correction circuit 36 in the present embodiment also include information corresponding to spectral characteristics of the image pickup device 21, in addition to information corresponding to an NA classification stored in the ROM 34E.

Therefore, according to the present embodiment, good color reproduction can also be realized in a case where image pickup device 21 that is mounted in the endoscope 2 is of a different classification.

(Third Embodiment)

Figure 10:
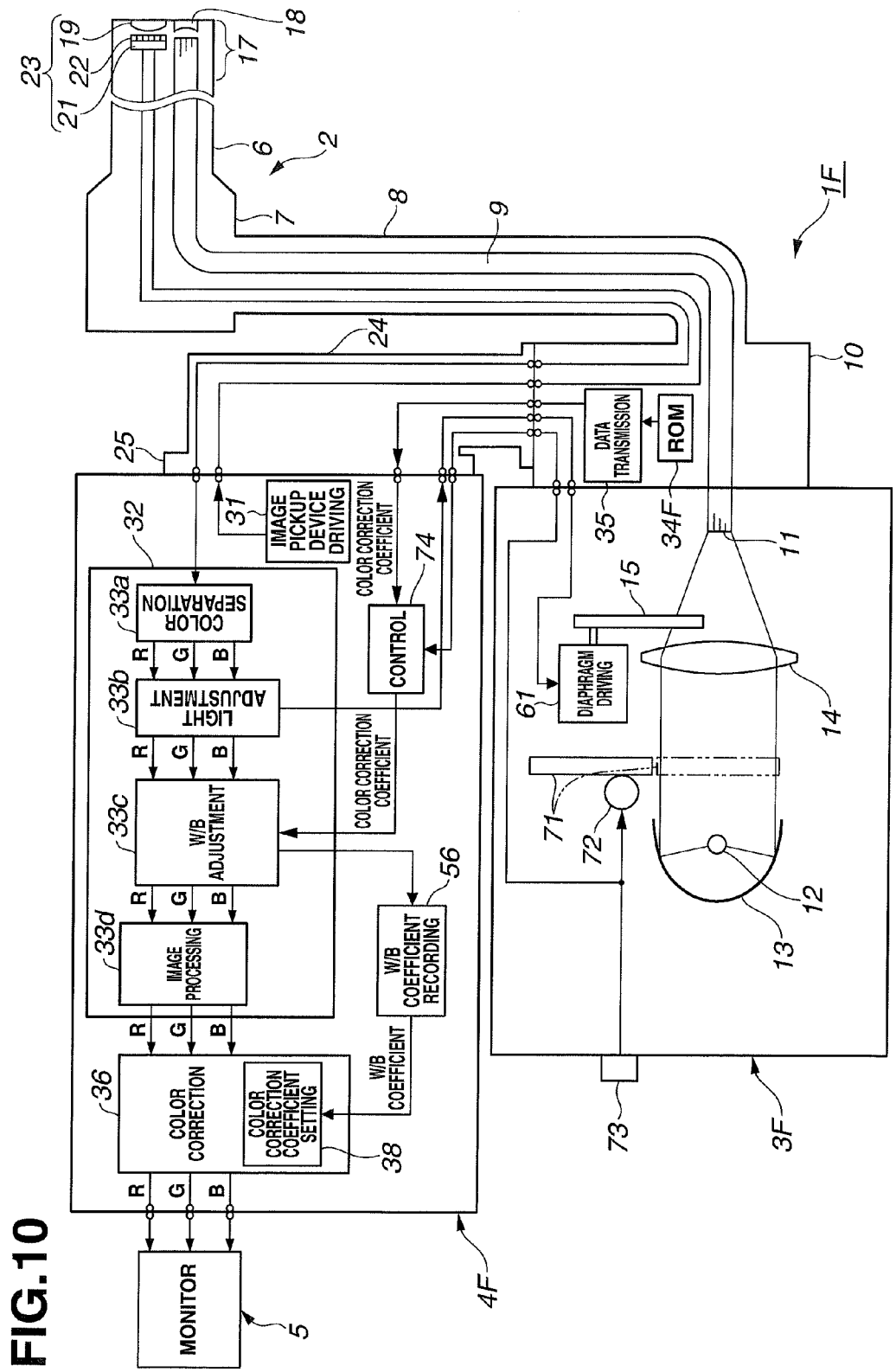
FIG. 10 is a view that illustrates an overall configuration of an endoscope apparatus according to a third embodiment of the present invention.

Next, a third embodiment of the present invention will be described. FIG. 10 shows an endoscope apparatus 1F according to a third embodiment of the present invention.

The above described embodiment is an endoscope apparatus having a normal observation mode that displays in color a normal color image picked-up by normal color pickup using illuminating light of a visible region on the monitor 5. In contrast, the present embodiment includes, in addition to the normal observation mode, a narrow-band light observation mode (NBI observation mode) that picks up an image under illumination of narrow-band illuminating light, and displays a narrow band image on the monitor 5.

Therefore, relative to the light source apparatus 3E in the endoscope apparatus 1E shown in FIG. 8, a light source apparatus 3F in the present endoscope apparatus 1F is further provided with a narrow-band filter 71 and a filter insertion/withdrawal mechanism 72 that uses a motor or the like that inserts the narrow-band filter 71 in an optical path or withdraws the narrow-band filter 71 therefrom.

The filter insertion/withdrawal mechanism 72 disposes the narrow-band filter 71 in the optical path or retracts the narrow-band filter 71 from the optical path in accordance with a mode selection signal from a mode selection switch 73 in response to a user operation. When a user selects the NBI observation mode by means of the mode selection switch 73, the narrow-band filter 71 is disposed in the optical path. When the narrow-band filter 71 is not disposed in the optical path, as shown in FIG. 11, the light source apparatus 3F supplies white color light having a spectral distribution of a wide band that spans the visible region (denoted by "B G R") to the light guide 9.

Figure 11:
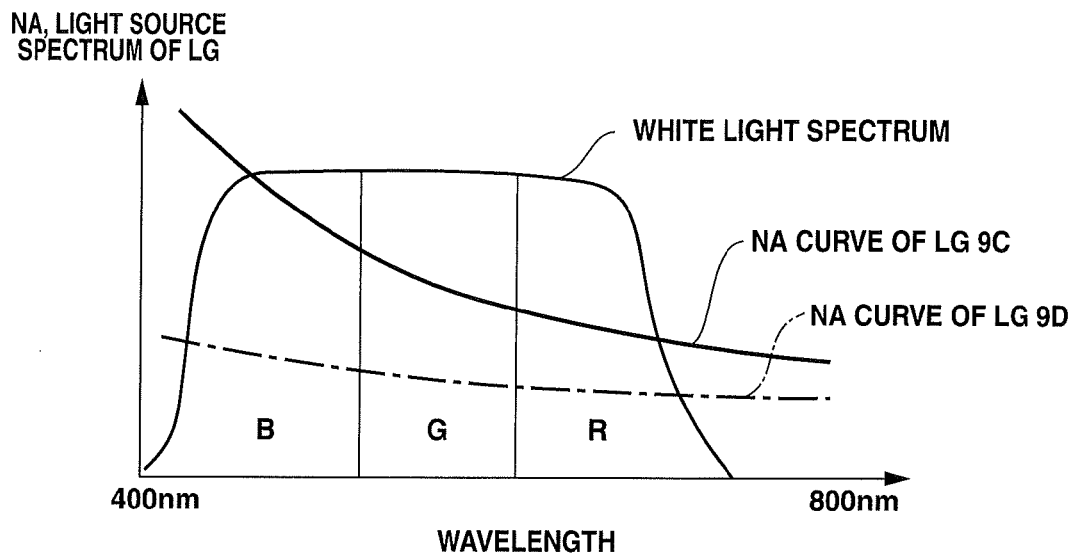
FIG. 11 is a view that illustrates an example of characteristics of a numerical aperture with respect to wavelengths of a light guide, and an example of the spectral distribution of white color light.
Figure 12:
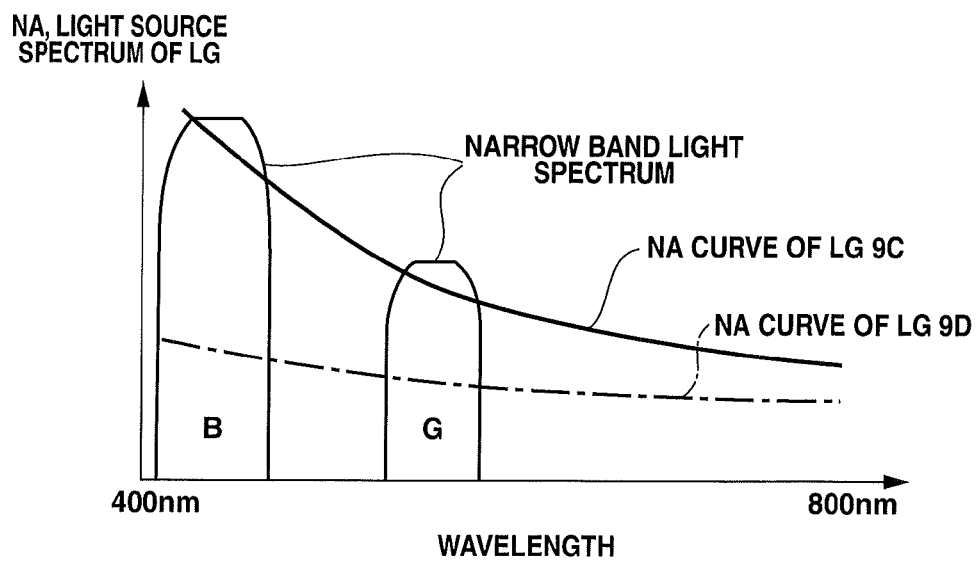
FIG. 12 is a view that illustrates an example of characteristics of a numerical aperture with respect to wavelengths of a light guide, and an example of the spectral distribution of narrow band light.

On the other hand, in a case where the narrow-band filter 71 is disposed in the optical path (indicated by a chain double-dashed line in FIG. 10), as shown in FIG. 12, for example, narrow band light that has a narrow band spectrum in the B and G wavelength regions is supplied to the light guide 9. In this connection, in FIG. 11 and FIG. 12, an example of the NA characteristics (NA curve on which an NA value changes according to the wavelength) of the light guides 9C and 9D is also shown.

As will be understood by comparing FIG. 11 and FIG. 12, because the spectral distributions of the light-source lights differ, the color balance of actual illuminating light that passes through the light guide and is emitted towards an object differs between the normal observation mode and the NBI observation mode in accordance with the NA characteristics of the light guide.

Consequently, in the present embodiment, a configuration is adopted that performs color correction that corresponds to each observation mode, respectively. Therefore, in addition to data for color correction coefficients in the normal observation mode, data for color correction coefficients in the NBI observation mode is also stored in a ROM 34F of the present embodiment, and a configuration is adopted that switches to and uses the color correction coefficients corresponding to the observation mode that is actually selected and used.

Therefore, the processor 4F has a control circuit 74 into which a mode selection signal of the mode selection switch 73 is inputted. The control circuit 74 performs control to output color correction coefficients corresponding to the mode selection signal to the white balance adjustment circuit 33c from among data for two kinds of color correction coefficients that is inputted from the data transmission section 35. The remaining configuration is the same as in FIG. 8.

Note that, the data for the color correction coefficients in the normal observation mode is the same as in the second embodiment. The operations in the normal observation mode are also the same as in the second embodiment.

In contrast, when the NBI observation mode is selected, because the illuminating light does not include illuminating light of a red wavelength region, it is sufficient for the color correction circuit 36 in the processor 4F to perform color correction processing with respect to G and B signals.

The white balance adjustment circuit 33c also performs white balance adjustment with respect to G and B signals. In this connection, in the present embodiment, white balance adjustment is also performed in the NBI observation mode in the same manner as in the normal observation mode.

Next, operations of the present embodiment will be described. The endoscopes 2C and 2D and the light guides 9C and 9D that are used in the second embodiment are used in the following description.

As described above, in the present embodiment, color correction coefficients for each observation mode are stored inside the ROM 34F as information storing means inside the endoscope 2. Note that, in the following description, although a case is described in which an R signal correction coefficient is also stored so that the present embodiment can also correspond to a case where red narrow band light is used as narrow band light for NBI observation, a configuration may also be adopted in which an R signal correction coefficient is not used in the color correction circuit.

The values of the signal correction coefficients are as described below. When the light guide 9C is mounted in the endoscope 2C, the B signal correction coefficient and R signal correction coefficient for white color observation of the light guide 9C, and the B signal correction coefficient and R signal correction coefficient for NBI observation of the light guide 9C are stored inside the ROM 34F. Likewise, when the light guide 9D is mounted in the endoscope 2D, the B signal correction coefficient and R signal correction coefficient for white color observation of the light guide 9D, and the B signal correction coefficient and R signal correction coefficient for NBI observation of the light guide 9D are stored inside the ROM 34F.

B signal correction coefficient for white color observation of light guide 9C=1.00

R signal correction coefficient for white color observation of light guide 9C=1.00

B signal correction coefficient for NBI observation of light guide 9C=1.00

R signal correction coefficient for NBI observation of light guide 9C=1.00

B signal correction coefficient for white color observation of light guide 9D=0.93

R signal correction coefficient for white color observation of light guide 9D=1.04

B signal correction coefficient for NBI observation of light guide 9D=0.89

R signal correction coefficient for NBI observation of light guide 9D=1.07

With respect to the equations that derive the above described color correction coefficients, $\alpha_B$ and $\alpha_R$ are the same values as in the second embodiment.

However, as shown in FIG. 11 and FIG. 12, the spectrums of light-source light are different for white color observation and NBI observation. In NBI observation in which the width of a wavelength band that is used is narrow, since a difference in the NA of the light guide 9 directly appears, according to the present embodiment, a value of $\beta=3.5$ is obtained by experiment for an equation that determines the B signal correction coefficient for NBI observation.

In this connection, although the variable $\beta$ is obtained by experiment based on optical characteristics, more specifically, the chromatic aberration, light distribution characteristics, and emitted light spectrum of the light source apparatus 3F, in general the value of $\beta$ increases as the light distribution of the light source widens and the light intensity of a center part becomes relatively lower. Further, as described above, $\beta$ increases as the width of the band of the spectrum of light-source light narrows. Therefore, the variable $\beta$ is set to an appropriate value in a range of approximately 1 to 5 in accordance with the optical characteristics of the light source apparatus 3F and the like. Further, the coefficients $\alpha_B$ and $\alpha_R$ are set in a range of approximately 1 to 1.2 and 0.9 to 1, respectively.

According to the present embodiment, when the normal observation mode is selected, the same advantageous effects as in the second embodiment can be obtained.

Further, when the NBI observation mode is selected, white balance adjustment and color correction that take into consideration a difference in the NA of the light guide 9 can be appropriately performed in accordance with the spectral distribution of light-source light supplied from the light source apparatus 3F in such case. Accordingly, when the NBI observation mode is selected also, even when a light guide that has a different NA value is used, a vascular structure in the vicinity of the epithelium of living tissue can be observed in detail in a state in which the color reproduction is good.

Note that a configuration may also be adopted so that, in the NBI observation mode, color correction coefficients are appropriately set with respect to an NA value or classification for two spectrums consisting of the g line and e line (or d line) of the light guide 9.

In this connection, a configuration may also be adopted that, for example, also stores information regarding the classification of the light source apparatus 3E or 3F that is actually connected to the endoscope 2 as data for color correction coefficients that is stored in the ROM 34F. Thus, the processor 4E or 4F may also be configured to perform color correction processing employing data for color correction coefficients that corresponds to the classification of the light source apparatus 3E or 3F that is actually being used together with the endoscope 2.

Further, for example, although an example is shown in FIG. 4 in which color correction is performed using the multiplication circuits 37a and 37c, the present invention is not limited to that example, and a dividing circuit, an amplifier in which the gain (amplification factor) can be varied, or an attenuator or the like may also be used.

Furthermore, for example, although examples are described above in which color correction is performed with respect to color signals such as an R signal and a B signal, a configuration may also be adopted that performs color correction with respect to a luminance signal and a color-difference signal.

Further, the foregoing embodiments and the like are not limited to a case in which the color correction circuit 36 is provided on the side that is after the video signal processing circuit 32 as shown, for example, in FIG. 1. For example, a configuration may be adopted in which color correction processing is performed with respect to an output signal of the color separation circuit 33a in FIG. 1. That is, a configuration may be adopted in which the color correction circuit 36 is provided in the video signal processing circuit 32 so as to perform color correction processing before performing image processing such as gamma correction and color tone correction. Thus, a configuration may be adopted so as to perform color correction processing without being affected by the characteristics of image processing. Furthermore, a configuration may be adopted in which the color correction circuit 36 is provided between the image processing circuit 33d and the white balance adjustment circuit 33c in FIG. 7.

A light source apparatus that is adopted according to the present invention is not limited to a light source apparatus in which a light source constituted by the light source lamp 12 and the condensing lens 14 are combined as described above, and the present invention can also be applied to a case in which a light emitting diode (LED) is used.

This is because, originally, the light distribution of an LED is wide due to diffused light of a phosphor, and for example, there is a difference in the light distribution of a phosphor that emits yellow color light and excitation light from a semiconductor that emits blue color light, and therefore even in the case of an optical system without a lens, an influence occurs that is caused by a color difference in a similar manner to the chromatic aberration described in the foregoing embodiments and the like.

Further, an embodiment that is configured by partially combining the above described embodiments or the like also belongs to the present invention.

The present invention is not limited to the foregoing embodiments, and various changes and improvements are possible within a range that does not depart from the gist of the present invention.

What is claimed is:

1. An endoscope apparatus, comprising:
   an endoscope in which an image pickup device and a light guide that emits an illuminating light are mounted;
   a signal processing apparatus to which the endoscope is detachably connected, and which performs signal processing with respect to an output signal of the image pickup device that is mounted in the endoscope that is connected; and
   a color correction section that performs color correction processing by performing multiplication between a color correction coefficient that is set based on a plurality of numerical apertures with respect to a plurality of different wavelengths included in a wavelength band of illuminating light of the light guide that is mounted in the endoscope that is connected, and at least one of signals of B, G and R generated by the signal processing apparatus,
   wherein, with respect to the color correction coefficient, taking as a reference a color signal of G among color signals of R, G and B that are generated based on an output signal of the image pickup device by the signal processing apparatus, color correction is performed using a condition of a coefficient of equation (3) to equation (5) below, respectively, by means of a B signal correction coefficient of equation (1) and an R signal correction coefficient of equation (2) below with respect to color signals of B and R:

$$B \text{ signal correction coefficient} = (NA_g/NA_e/\alpha_B)^\beta \quad (1)$$

$$R \text{ signal correction coefficient} = (NA_c/NA_e/\alpha_R)^\beta \quad (2)$$

$$1 \leq \alpha_B \leq 1.2 \quad (3)$$

$$0.9 \leq \alpha_R \leq 1 \quad (4)$$

$$1 < \beta \leq 5 \quad (5)$$

where, $NA_g$, $NA_e$ and $NA_c$ represent a numerical aperture of a light guide at a g line, an e line, and a C line, respectively; $\alpha_B$ and $\alpha_R$ represent coefficients that are set based on $NA_g$, $NA_e$ and $NA_c$ of a light guide that serves as a reference; and $\beta$ represents a coefficient that is set in accordance with an optical characteristic of a light source apparatus to which the endoscope is connected.

2. The endoscope apparatus according to claim 1, wherein:
   the signal processing apparatus has a white balance adjustment section that performs white balance adjustment so as to achieve white balance among relative levels of a plurality of color signals that are generated based on an output signal of the image pickup device; and
   the color correction coefficient is used for setting a target value for white balance adjustment of the white balance adjustment section.

3. The endoscope apparatus according to claim 2, further comprising:
   a light source apparatus that supplies light-source light for emitting the illuminating light to the light guide, and a diaphragm that is provided in the light source apparatus and that varies a light amount of the light-source light that is supplied to the light guide;
   wherein, in a state of a light amount at a time of observation that is different from a light amount at a time of the white balance adjustment, the color correction section preliminarily sets the color correction coefficient so as to become a target value that is required to perform white balance adjustment of the relative levels of the plurality of color signals.

4. The endoscope apparatus according to claim 1, comprising:
   a first observation mode that performs a color image pickup operation under white color illuminating light; and
   a second observation mode that performs an image pickup operation under a wavelength band that is different from the white color illuminating light;
   wherein:
   the color correction coefficient is set for the first and second observation modes, respectively; and
   the color correction section performs color correction processing that switches the color correction coefficient in response to switching of an observation mode.

5. The endoscope apparatus according to claim 1, further comprising an information storage section that stores data of the color correction coefficient and outputs the data to the color correction section.

* * * * *